(12) United States Patent
Suzuki et al.

(10) Patent No.: US 8,263,791 B2
(45) Date of Patent: Sep. 11, 2012

(54) METHOD AND REAGENT FOR PROTEIN ANALYSIS

(75) Inventors: Yoshio Suzuki, Tokyo (JP); Kenji Yokoyama, Ibaraki (JP); Nobuyuki Takagi, Kanagawa (JP); Tomoyuki Chimuro, Kanagawa (JP); Atsushi Shinohara, Saitama (JP)

(73) Assignees: National Institute of Advanced Industrial Science and Technology, Tokyo (JP); Kanto Kagaku Kabushiki Kaisha, Tokyo (JP)

( * ) Notice: Subject to any disclaimer, the term of this patent is extended or adjusted under 35 U.S.C. 154(b) by 393 days.

(21) Appl. No.: 12/492,583

(22) Filed: Jun. 26, 2009

(65) Prior Publication Data
US 2010/0000865 A1 Jan. 7, 2010

(30) Foreign Application Priority Data
Jul. 7, 2008 (JP) ................................. 2008-177104

(51) Int. Cl.
*C07D 313/00* (2006.01)

(52) U.S. Cl. ......... 549/416; 549/200; 549/356; 204/461

(58) Field of Classification Search .......... 204/456–467; 549/13, 346, 415, 200, 208, 356, 416, 425
See application file for complete search history.

(56) References Cited

U.S. PATENT DOCUMENTS

| | | | |
|---|---|---|---|
| 4,145,215 A | 3/1979 | Van Allan et al. | |
| 4,322,487 A | 3/1982 | Merrill et al. | |
| 4,704,198 A * | 11/1987 | Ebersole et al. | 204/469 |
| 7,238,792 B2 | 7/2007 | Li et al. | |
| 2004/0224372 A1 * | 11/2004 | Li et al. | 435/7.92 |
| 2009/0045060 A1 | 2/2009 | Suzuki et al. | |

FOREIGN PATENT DOCUMENTS

| | | |
|---|---|---|
| JP | 2007-114009 | 5/2007 |
| WO | WO 2006/132030 A1 | 12/2006 |
| WO | WO 2007/046537 A1 | 4/2007 |

OTHER PUBLICATIONS

Machine translation of JP 2007-114009.*
Suzuki, Y., and K. Yokoyama, "Design and sythesis of ICT-based fluorescent probe for high-sensitivity protein detection and application to rapid protein staining for SDS-PAGE", Proteomics, vol. 8, Jul. 14, 2008, p. 2785-2790.*
Wei Wang, et al., "Design and Synthesis of Efficient Fluorescent Dyes for Incorporation into DNA Backbone and Biomolecule Detection" Bioconjugate Chemistry, vol. 18. No. 4. May 18, 2007. pp. 1036-1052.

* cited by examiner

*Primary Examiner* — J. Christopher Ball
(74) *Attorney, Agent, or Firm* — Oblon, Spivak, McClelland, Maier & Neustadt, L.L.P.

(57) ABSTRACT

A convenient, rapid, and highly sensitive protein detection method is provided. According to the present invention, an easily water-soluble compound of formula I is provided:

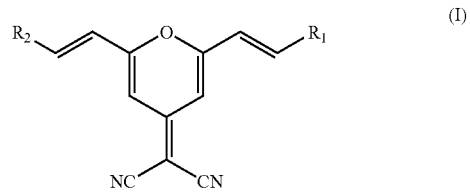

(I)

[wherein, $R_1$ and $R_2$ are same or different, each of which is an aryl or heteroaryl group substituted with one or more anionic substituents].

16 Claims, 3 Drawing Sheets

(A) ovotransferrin, (B) albumin, (C) ovalbumin, (D) carboanhydrase,
(E) myoglobin, (F) cytochrome C

| Lane | 1 | 2 | 3 | 4 | 5 | 6 | 7 | 8 | 9 | 10 |
|---|---|---|---|---|---|---|---|---|---|---|
| Protein (ng/band) | 167 | 83.3 | 41.7 | 20.8 | 10.4 | 5.2 | 2.6 | 1.3 | 0.7 | 0.4 |

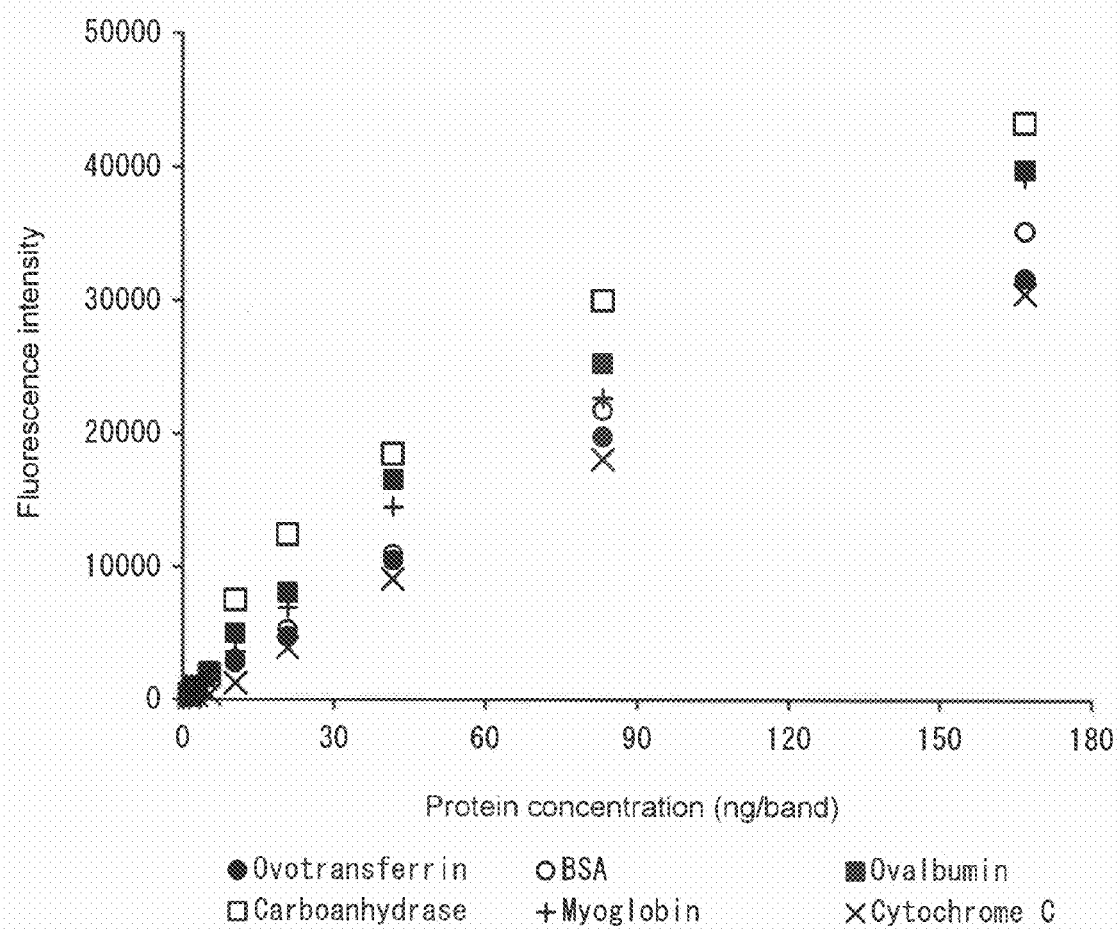

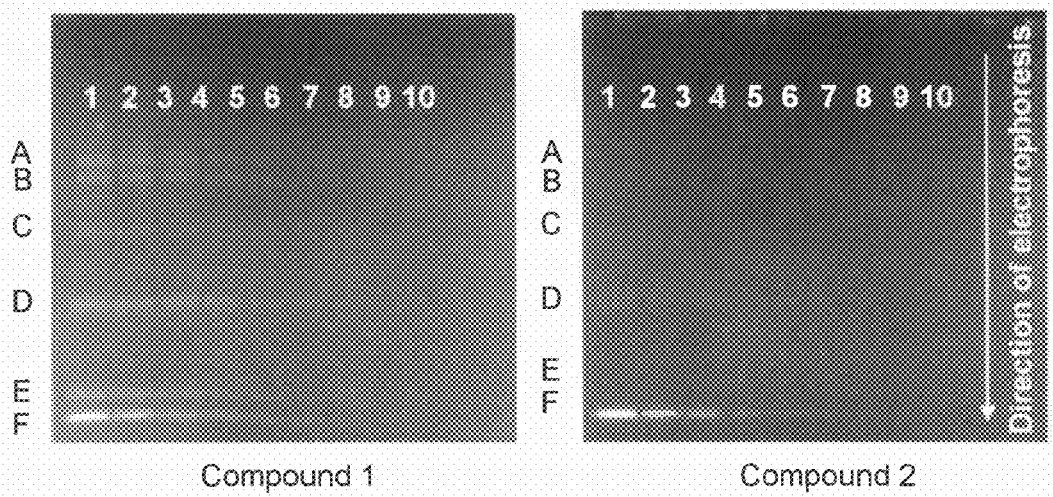

METHOD AND REAGENT FOR PROTEIN ANALYSIS

BACKGROUND OF THE INVENTION

1. Field of the Invention

The present invention relates to a method for protein analysis using a water soluble fluorescent compound and the use of the compound as a protein analysis reagent.

2. Background Art

As a method for protein analysis, an electrophoretic methods are widely employed. The electrophoretic methods are advantageous in that these allow proteins to be resolved based on their molecular weights so that the molecular weights can be estimated, these enable semi-quantitative measurement of amounts of proteins, and the methods can be carried out using a relatively simple apparatus, for example.

Examples of a technique for protein analysis using electrophoresis include a technique that involves staining proteins existing in a sample before electrophoresis or directly staining proteins existing on electrophoresis carriers such as gel and then visually detecting the proteins, a technique that involves transferring proteins to an appropriate membrane from electrophoresis carriers and then carrying out protein staining, antibody staining, or the like (e.g., western blotting), and a technique that involves staining proteins existing on electrophoresis carriers, excising a band containing a desired protein and subsequently subjecting the resultant to mass spectroscopy.

Examples of a method for protein staining include a CBB (Coomassie brilliant blue) staining method, a silver staining method, and a Sypro Ruby staining method.

Among these conventional techniques, the CBB method can be carried out conveniently and rapidly, but it has problems that its detection sensitivity is low (detection limit: 50 ng to 100 ng) and its detection sensitivity varies significantly depending on protein type. The silver staining method is a highly sensitive method such that the detection limit ranges from 1 ng to 10 ng, but it has drawbacks in that it cannot be quantitative and requires special processing of a waste solution containing silver. A method using a fluorescent dye such as Sypro Ruby (Invitrogen Corporation) may exhibit higher detection sensitivity than that of the silver staining method; however, when the method is applied to SDS-PAGE, such fluorescent dye tends to be affected by SDS remaining on the carriers, so that a target protein cannot be detected in some cases. Moreover, because of relatively high background, fixation should be carried out before staining proteins with a fluorescent dye as well as washing and decoloration should be carried out for a sufficient period of time after staining. Accordingly, the method has problems that it cannot be performed rapidly and leads to a significant burden on operators.

To solve the above problems with conventional methods for protein staining, the present inventors have searched for novel compounds that can be used for protein staining (International Patent Publication No. WO2006/132030 Pamphlet and JP Patent Publication (Kokai) No. 2007-114009 A). As a result, fluorescent compounds have been obtained that form complexes with proteins via hydrophobic bonds and exhibit a constant rate of color development regardless of protein type (International Patent Publication No. WO2006/132030 Pamphlet). Also, a method for protein detection for electrophoresis has been developed, by which the fluorescent compounds are dissolved in electrophoretic buffers for SDS-PAGE, so as to allow simultaneous performance of protein resolving and protein staining (JP Patent Publication (Kokai) No. 2007-114009 A).

However, all of the fluorescent compounds specifically described in the Examples of the above documents are hardly soluble in water, so that insoluble matter is frequently formed during staining and storage. Therefore, insoluble matter is deposited on electrophoresis carriers and then false positive spots appear during the detection step, which may disturb the detection.

SUMMARY OF THE INVENTION

Conventional methods for protein staining each have problems as described above. Hence, easily handled reagents for protein staining and convenient and rapid methods for protein staining are still required.

As a result of intensive experiments to solve the above problems concerning protein staining, the present inventors have discovered a compound that can be used for protein staining and has high water solubility. With the use of this compound, proteins can be detected successfully regardless of protein type. Furthermore, since the compound is water soluble, it has high handleability.

The present invention has the following features.

(1) An easily water-soluble fluorescent compound of formula I or a salt thereof:

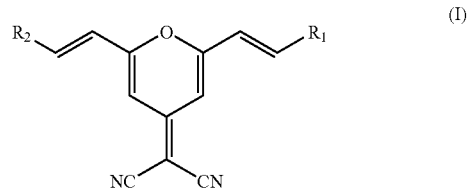

[wherein $R_1$ and $R_2$, which may be same or different, are an aryl or heteroaryl group substituted with one or more anionic substituents].

(2) The compound according to (1) above wherein the compound is represented by formula Ia:

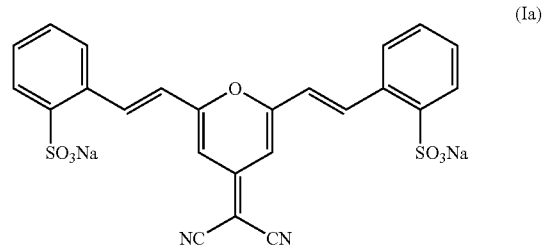

(3) A method for analyzing proteins, which comprises detecting proteins using the compound according to (1) or (2) above, thereby analyzing the proteins qualitatively or quantitatively.

(4) The method according to (3) above, which comprises resolving proteins by electrophoresis.

(5) The method according to (4) above, which comprises the steps of:
resolving proteins by electrophoresis on a carrier; and
immersing the electrophoresis carrier in an aqueous solution containing the compound according to (1) or (2) above.

(6) The method according to (4) above, wherein a buffer containing the compound according to (1) or (2) above is used as a buffer for electrophoresis.

(7) The method according to any one of (3) to (6) above, wherein a solution containing the compound according to (1) or (2) above and a solution containing a detergent are used.
(8) The method according to (7) above, wherein the detergent is a nonionic surfactant.
(9) The method according to (7) above, wherein the detergent is a fatty acid polyoxyethylene sorbitan-based surfactant.
(10) A reagent for protein analysis containing the compound according to (1) or (2) above.

The present invention makes it possible to conveniently and rapidly perform highly sensitive qualitative or quantitative protein analysis.

BRIEF DESCRIPTION OF THE DRAWINGS

FIG. 2 shows a graph representing the relationship between the concentrations of proteins each composing a band and fluorescence intensity, as observed from fluorescent images in FIG. 1.
FIG. 3 shows fluorescent images of electrophoresis carriers, for which staining was carried out simultaneously with electrophoresis.
Concentration of fluorescent compound: 15 μg/mL; left: compound 1; right: compound 2; excitation wavelength: 525 nm; and cut filter: 550 nm.

DESCRIPTION OF THE PREFERRED EMBODIMENTS

Figure 1:
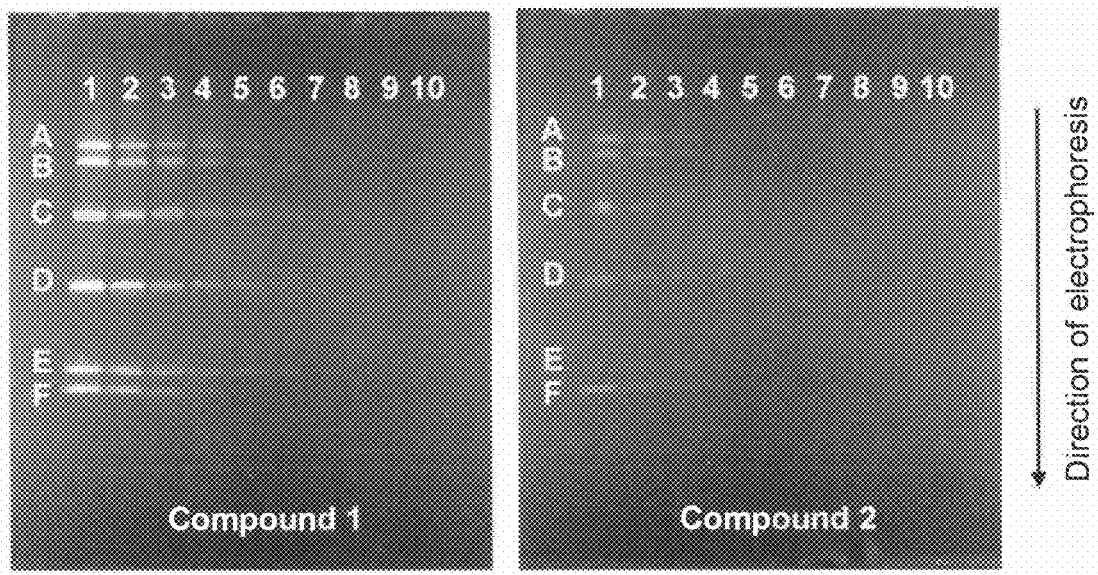
FIG. 1 shows fluorescent images of electrophoresis carriers.
Concentration of fluorescent compound: 100 μg/mL; left: compound 1; right: compound 2; excitation wavelength: 525 nm; and cut filter: 550 nm.

The present invention relates to a water soluble fluorescent compound useful for protein analysis, a method for protein analysis using the compound, and the use of the compound as a protein analysis reagent.

In the present invention, the term "analysis" of proteins includes qualitative detection of proteins, that is, confirmation of the presence or the absence of proteins; measurement of the molecular weights of proteins; determination of the distribution of proteins; quantitative measurement of proteins; and the like.

In this specification, the term "water soluble" or "easily water-soluble" refers to a property of the relevant substance such that: it is soluble in water at room temperature or lower at a certain concentration such as 100 μg/mL or higher; and it is almost never or never precipitated during operation.

The fact that a compound that can be used for protein staining is hardly soluble in water causes deposition of insoluble matter at sites at which no protein exists when a protein on an electrophoresis carrier is stained, for example. This causes the formation of false positive spots and thus extremely adversely affects the accuracy of the detection results. If a compound that can be used for protein staining is water soluble, excessive compounds that have not participated in reaction (interaction) between the protein and the compound can be easily removed after reaction by washing with water, a buffer, or the like. In other words, the fact that such compound is water soluble enables precise detection of a protein and is highly advantageous for the purpose of protein staining.

Also, if such compound is water soluble, when a reagent erroneously places on hands, gloves, clothing, and the like during the process for protein staining, it can be easily removed by washing with water. Therefore, the fact that such compound is water soluble is highly advantageous in terms also of safety and health during operation.

In this specification, the term "fluorescence" refers to the property of generating light (fluorescence) with a maximum wavelength that is typically longer than that of irradiated light (exciting light) when the light with a specific wavelength is irradiated. The maximum fluorescence wavelength of a fluorescent compound to be used in the present invention is not particularly limited, but ranges from 450 nm to 550 nm, for example. Fluorescence can be measured using various instruments. For example, measurement can be carried out using a commercially available fluorescence imaging analyzer (available from ATTO Corporation, TECAN GROUP LTD., GE HEALTHCARE BIO-SCIENCES, and the like).

In an aspect, the present invention relates to an easily water-soluble fluorescent compound of formula I or a salt thereof:

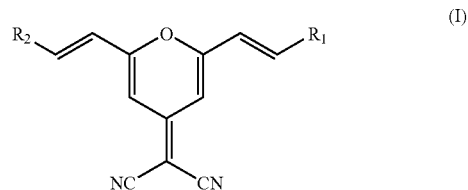

(I)

[wherein, $R_1$ and $R_2$ are same or different, each of which is an aryl or heteroaryl group substituted with one or more anionic substituents]

In the present invention, examples of "anionic substituent" include a sulfonic acid group, a carboxyl group, a phosphate group, or salts thereof (e.g., a lithium salt, a sodium salt, a potassium salt, a rubidium salt, a cesium salt, an ammonium salt, and a quaternary ammonium salt having a linear or branched alkyl group having 1 to 10 carbon atoms, which may have a substituent). Preferably, an anionic substituent is a sulfonic acid group or a salt thereof (e.g., a sodium salt).

Examples of an aryl group include $C_6$ to $C_{20}$ aromatic hydrocarbon groups (e.g., a phenyl group, a tolyl group, a benzyl group, a xylyl group, a naphthyl group, an anthryl group, a pyrenyl group, and a biphenyl group), which may have substituents other than the above anionic substituents.

Examples of a heteroaryl group include, $C_5$ to $C_{20}$ heterocyclic compounds (e.g., a pyridyl group, a bipyridyl group, a furyl group, a carbazolyl group, a thienyl group, a pyrrolyl group, an oxazolyl group, and a quinolinyl group) which may have substituents other than the above anionic substituents.

The fluorescent compound of the present invention preferably has a structure of the following formula Ia:

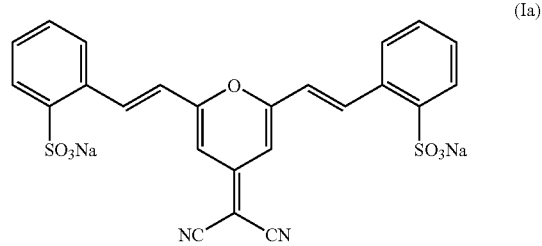

(Ia)

Furthermore, the present invention also relates to a method for protein analysis using a compound of the above formula I, and preferably the above formula Ia.

A specific embodiment for protein detection using the method of the present invention comprises the steps of, for example: (i) resolving a sample containing proteins by electrophoresis and then immersing an electrophoresis carrier such as gel in an aqueous solution containing the fluorescent compound of the present invention, such that the fluorescent compound can react with the proteins on the carrier; and (ii) immersing the electrophoresis carrier in water, an appropriate buffer, or the like, thereby removing excessive fluorescent compounds that have not interacted with the protein (decoloration and washing step). Before contacting the carrier with the fluorescent compound, the carrier may be immersed in a solution with a specific composition (e.g., an aqueous solution containing 1% Tween80) for a certain period of time (e.g., 10 to 30 minutes).

An aqueous solution containing the fluorescent compound of the present invention (hereinafter, may be simply referred to as "an aqueous solution of the compound") is typically a buffer, which is adjusted at preferably pH 1 to 4, and more preferably pH 2 to 3. The aqueous solution may also contain alcohol. Alcohol is not limited, as long as it is highly soluble in water or a buffer, and is preferably $C_1$ to $C_4$ alcohol and more preferably $C_1$ to $C_3$ alcohol. A buffer may be any buffer that is generally used in the art, such as a phosphate buffer, a citrate buffer, a glycine buffer, a Tris-glycine buffer, a Tris buffer, and a MOPS buffer. A liquid to be used for removing excessive fluorescent compounds can be water, an aqueous solution of a detergent, the examples of which are listed below, or a buffer of the above listed buffers.

The time for immersion in step (i) above ranges from, for example, 5 to 60 minutes, is preferably 30 minutes or less, and is more preferably approximately 10 minutes. The time for removing excessive fluorescent compounds in step (ii) above ranges from, for example, 10 to 100 minutes, preferably 20 to 60 minutes, and more preferably 30 to 40 minutes.

Surprisingly, the present inventors have discovered that the time necessary for decoloration in step (ii) above can be drastically shortened by immersing of a carrier in an aqueous solution containing a detergent before and after immersion of the carrier in an aqueous solution containing the compound of the present invention.

Therefore, in a preferred embodiment, the method of the present invention comprises the steps of: immersing an electrophoresis carrier in an aqueous solution containing the fluorescent compound; and immersing the same in an aqueous solution containing a detergent. If the time for processing a carrier after electrophoresis is long, proteins resolved by electrophoresis are diffused within the carrier, which can adversely affect the detection results. Accordingly, it is highly advantageous that the time for removing excessive fluorescent compounds can be shortened not only as it makes it possible to obtain the results rapidly by shortening the time needed, but also as it provides more precise analytical results.

A detergent that is used in the present invention is not particularly limited and is preferably a nonionic surfactant, more preferably a fatty acid polyoxyethylene sorbitan-based surfactant, and most preferably Tween80 (polyoxyethylene sorbitan monooleate) or Tween20 (polyoxyethylene sorbitan monolaurate). The concentration of such detergent in an aqueous solution is, for example, 0.1% (v/v), 0.5% (v/v), 1% (v/v), 2% (v/v), 3% (v/v), 4% (v/v), or 5% (v/v) and preferably 1% (v/v).

Alternatively, the method of the present invention can also be carried out by achieving interaction between the compound of the present invention and a protein simultaneously with electrophoresis through addition of the compound of the present invention to a buffer for electrophoresis instead of immersing an electrophoresis carrier in the fluorescent compound aqueous solution after electrophoresis. In this case, since only the step of removing excessive fluorescent compounds on the carrier is required after completion of electrophoresis, the time from the completion of electrophoresis to measurement can be shortened. This is highly advantageous as described above not only in that it makes it possible to rapidly obtain results by shortening the time needed, but also in that it provides more precise analytical results.

In this specification, examples of an "electrophoresis carrier" or a "carrier" are not particularly limited, as long as they are generally used for electrophoresis, including membranes (e.g., a cellulose acetate membrane, a nitrocellulose membrane, and a poly-vinylidenedifluoride (PVDF) membrane) and gel (e.g., polyacrylamide gel and agarose gel). Preferably, a carrier is gel and is particularly SDS-polyacrylamide gel.

Alternatively, the method of the present invention can also be carried out by contacting a protein in a sample with the compound of the present invention and then carrying out electrophoresis.

Furthermore, the method of the present invention can also be applied for protein analysis methods not employing electrophoresis, such as an immunoprecipitation method and a dot-blot method.

In another aspect, the present invention relates to the use of an easily water-soluble fluorescent compound of formula I for protein detection:

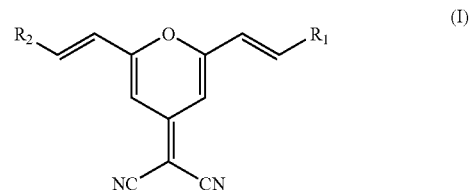

(I)

[wherein $R_1$ and $R_2$, which may be same or different, are an aryl or heteroaryl group substituted with one or more anionic substituents].

The compound of the formula I has preferably a structure of the following formula Ia:

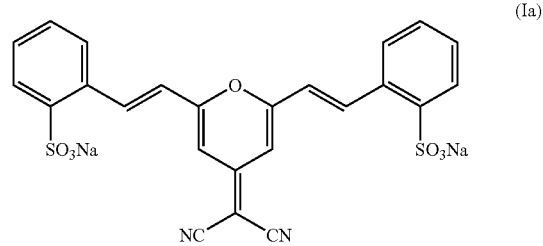

(Ia)

The compound of the formula I of the present invention can be synthesized by, for example, a method comprising the steps of: in an appropriate solvent (e.g., ethanol/methanol=1:1 (v/v)), reacting aldehyde having an $R_1$ and/or $R_2$ group with 4-(dicyanomethylene)-2,6-dimethyl-4H-pyrane at a molar ratio of 1 to 2 or more: 1 in the presence of an appropriate catalyst (e.g., a base such as piperidine) under an argon atmosphere at 70° C. to 120° C. for 1 to 24 hours (aldol condensation); and recovering and then purifying the subsequently obtained products. Products can be purified by an appropriate combination of techniques such as crystallization, HPLC, TLC, and silica gel chromatography, for example.

A target compound can be identified by an appropriate combination of measuring methods such as NMR, IR, UV, mass spectroscopy, and elementary analysis.

According to a specific embodiment, the present invention further provides the use of the compound of the above formula I (preferably, formula Ia) as a reagent for protein analysis. Preferably, protein analysis is carried out by electrophoresis.

The present invention further relates to a reagent for protein analysis containing the compound of the present invention. The present invention also relates to a kit for protein analysis comprising as a component a reagent containing the compound of the present invention. The kit may comprise as a further component a buffer, a gel for electrophoresis for resolving proteins and the like.

The present invention is hereafter described in greater detail with reference to the following examples, although the scope of the present invention is not limited thereto.

EXAMPLE 1

(Example 1) Synthesis of Compound 1

(2,2'-(1E,1'E)-2,2'-(4-(dicyanomethylene)-4H-pyrane-2,6-diyl)bis(ethene-2,1-diyl)bis(sodium benzenesulfonate)salt)

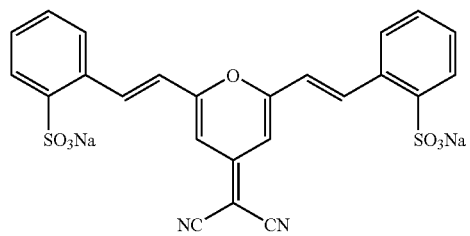

Sodium 2-sulfo benzaldehyde (2.42 g (11.6 mmol)) was added to a 50-mL three-neck flask and then suspended in 30 mL of ethanol:methanol=1:1 (v/v). 4-(dicyanomethylene)-2,6-dimethyl-4H-pyrane (1.0 g (5.81 mmol)) and piperidine (495 mg (5.81 mmol)) were added and then the resultant was refluxed under an argon atmosphere for 12 hours. The precipitate was collected by filtration. The thus obtained yellow powder was washed with water and then subjected to drying under reduced pressure, so that 1.43 g of a desired compound was obtained (yield: 44.5%).

ESI-MS (+): $[M+Na—H]^+=574.6$ $^1$H-NMR (400 MHz, DMSO-d6) σ 6.92 (2H, s), 7.20 (2H, d, J=16 Hz), 7.37-7.46 (4H, m), 7.77-7.88 (4H, m), 8.62 (2H, d, J=16 Hz).

$^{13}$C-NMR (100.53 MHz, DMSO-d6) σ 56.6, 106.5, 115.5, 120.3, 127.2, 127.4, 129.0, 129.3, 132.5, 138.1, 146.4, 156.1, 159.7.

(Comparative Example 1) Synthesis of Compound 2

((E)-2-(2-(4-(dicyanomethylene)-6-methyl-4H-pyrane-2-yl)vinyl)sodium Benzenesulfonate

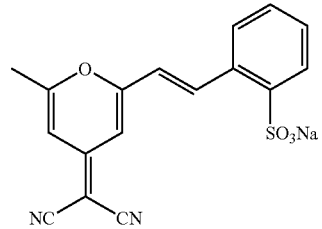

Sodium 2-sulfo benzaldehyde (2.0 g (9.61 mmol)) was added to a 200-mL three-neck flask and then suspended in 120 mL of ethanol:methanol=1:1 (v/v). 4-(dicyanomethylene)-2,6-dimethyl-4H-pyrane (5.0 g (29.0 mmol)) and piperidine (818 mg (9.61 mmol)) were added and then the resultant was refluxed under an argon atmosphere for 3 hours. The precipitate was resolved by filtration and then the mother liquor was concentrated. The thus obtained precipitate was washed with ethyl acetate and then the resultant was dried under reduced pressure, so that 1.49 g of a desired compound was obtained (yield: 42.8%).

ESI-MS(+): $[M+Na—H]_+=384.8$ $^1$H-NMR (400 MHz, DMSO-d6) σ 2.45 (3H, s), 6.72 (1H, dd, J=0.91, 2.3 Hz), 6.94 (1H, d, J=2.3 Hz), 7.23 (1H, d, J=16 Hz), 7.34-7.42 (2H, m), 7.79-7.84 (2H, m), 8.63 (1H, d, J=16 Hz).

$^{13}$C-NMR (100.53 MHz, DMSO-d6) σ 19.5, 55.8, 106.0, 107.3, 115.4, 119.3, 126.4, 127.1, 129.0, 129.1, 132.1, 137.3, 147.0, 156.8, 160.2, 164.1.

(Comparative Example 2) Synthesis of Compound 3

((E)-2-(2-(4-hydroxynaphthalene-1-yl)vinyl)-6-methyl-4H-pyrane-4-ylidene)malononitrile)

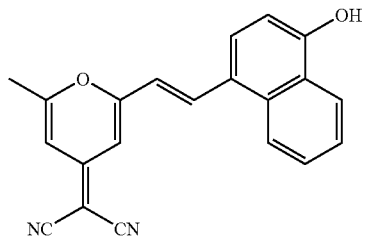

4-hydroxy-1-naphtaldehyde (0.70 g (5.81 mmol)), 4-(dicyanomethylene)-2,6-dimethyl-4H-pyrane (1.0 g (5.81 mmol)), piperidine (0.50 g (5.81 mmol)), and ethanol (50 mL) were added to a 50-mL three-neck flask. The resultant was heated and refluxed under an argon atmosphere for 6 hours and then the solvent was removed under reduced pressure, followed by purification by column chromatography (SiO$_2$, CHCl$_3$:MeOH=10:1 (v/v)). Thus a desired compound was obtained (yield: 48.2%).

ESI-MS(+): $[M+Na]^+=349.1$ $^1$H-NMR (400 MHz, CDCl$_3$, r.t., TMS, δ/ppm) 1.71 (s, 3H), 5.27 (s, 1H), 5.51 (s, 1H), 6.65 (d, 1H), 6.85 (d, 1H), 6.59 (d, 1H), 7.21 (d, 1H), 7.35 (t, 1H), 7.38 (t, 1H), 8.08 (d, 1H).

EXAMPLE 2

Measurement of Maximum Absorption Wavelength and Maximum Fluorescence Wavelength Compound 1 and Compound 2 were separately dissolved in purified water at a concentration of 25 μg/mL. The absorption spectra at a wavelength ranging from 200 nm to 800 nm and the fluorescence spectra at a wavelength ranging from 450 nm to 600 nm were measured. The absorption spectra were measured using U3310 (Hitachi High-Technologies Corporation) and the fluorescence spectra were measured using RF-1500 (Shimadzu Corporation). The results are shown in Table 1.

TABLE 1

Comparison of optical characteristics of compounds

| | Maximum absorption wavelength | Maximum fluorescence wavelength |
| --- | --- | --- |
| Compound 1 | 293 nm<br>380 nm | 516 nm (excitation: 444 nm) |
| Compound 2 | 388 nm | 511 nm (excitation: 440 nm) |

EXAMPLE 3

Protein Detection (1) Preparation of Samples

Two (2) mL of a stock buffer (a mixture of purified water (4.2 mL), 0.5 M Tris-hydrochloric acid buffer (pH 8.6) (1.0 mL), glycerol (0.8 mL), 100 g/L sodium dodecyl sulfate (1.6 mL), and 2-mercaptoethanol (0.4 mL)) was added to 2 mg of a commercially available molecular weight marker (Protein Standard Mixture IV; Merck & Co., Inc.). The mixture was heated in boiling water for 2 minutes and then cooled. Thirty (30) μL each of the resultant was dispensed in a 0.5-mL microtube and then cryopreserved at −80° C. until the use thereof. A sample diluent (a mixture of purified water (3.8 mL), 0.5 M Tris-hydrochloric acid buffer (pH 8.6) (1.0 mL), glycerol (0.8 mL), 100 g/L sodium dodecyl sulfate (1.6 mL), and 5 g/L bromophenol blue (0.8 mL)) was added to the thawed molecular weight marker, so that a dilution series with protein concentrations ranging from 0.4 ng/μL to 200 ng/μL was prepared.

The marker contained, in terms of mass, equal amounts of ovotransferrin (78 kDa), albumin (66.3 kDa), ovalbumin (42.7 kDa), carboanhydrase (30 kDa), myoglobin (16.9 kDa), and cytochrome C (12.4 kDa).

(2) Protein Resolving and Detection by Electrophoresis

Conditions for electrophoresis are as follows:

Electrophoresis apparatus: RAPIDAS-Mini-Slab electrophoresis chamber AE6450 (ATTO Corporation)
Polyacrylamide gel: Multigel II mini 10/20 (13W) (COSMO BIO Co., Ltd.)
Buffer for electrophoresis: 27.2 mM Tris (hydroxymethyl) aminomethane, 192 mM glycine, 3.5 mM Sodium dodecyl sulfate (pH 8.3)
Fluorescence imaging analyzer: Light capture II (ATTO Corporation)
Light source: green LED (center wavelength: 525 nm)
Cut filter: R-60 (550 nm).

Each sample of the dilution series prepared in (1) above was applied to a gel at 5 μL/well (lane 1: 167 ng of protein/band; lane 2: 83.3 ng/band; lane 3: 41.7 ng/band; lane 4: 20.8 ng/band; lane 5: 10.4 ng/band; lane 6: 5.2 ng/band; lane 7: 2.6 ng/band; lane 8: 1.3 ng/band; lane 9: 0.7 ng/band; and lane 10: 0.4 ng/band) and then subjected to electrophoresis with constant current of 30 mA for 45 minutes.

After electrophoresis, the gel was immediately immersed in a solution (I) (purified water, 1% Tween80 aqueous solution, or 1% Tween20 aqueous solution) for a predetermined period of time (20 minutes or 30 minutes). Subsequently, the gel was transferred to another container and then a buffer (purified water/25 mM phosphate buffer (pH 2.5)/methanol=45/45/10 (v/v)) in which Compound 1 (100 μg/mL) had been dissolved was added. After being left to stand for 10 minutes, the gel was transferred to another container and then immersed in a solution (II) (purified water, 1% Tween80 aqueous solution, or 1% Tween20 aqueous solution) for decoloration. The state of the gel was observed with time using a fluorescence imaging analyzer and then the time needed to detect the bands each of which contains 5 to 10 ng of protein/band (corresponding to the detection limit in the case of silver staining) of lanes (lane 5 and lane 6) was measured. During staining, no precipitation of Compound 1 was observed in the solutions.

The results of the times needed (the time from the completion of electrophoresis to the completion of decoloration) and detection sensitivity under various conditions are shown in Table 2.

TABLE 2

Conditions for treatment with analysis reagents and results

| | Conditions 1 | Conditions 2 | Conditions 3 | Conditions 4 | Conditions 5 |
| --- | --- | --- | --- | --- | --- |
| Solution (I) | Purified water | Tween80 | Purified water | Tween80 | Tween20 |
| Time for treatment | 30 minutes | 20 minutes | 30 minutes | 20 minutes | 20 minutes |
| Solution (II) | Purified water | Purified water | Tween80 | Tween80 | Tween20 |
| Time for treatment | 60 minutes | 30 minutes | 30 minutes | 30 minutes | 40 minutes |
| Total time needed | 100 minutes | 60 minutes | 70 minutes | 60 minutes | 70 minutes |
| Detection sensitivity | 5 ng | 5 ng | 5 ng | 5 ng | 10 ng |

When treatment before staining and decoloration were carried out with purified water, the total time needed was 100 minutes. However, the time needed could be drastically shortened by the addition of the detergent to the solution (I) or (II).

EXAMPLE 4

Evaluation of Protein Detection Using Compound 1 and Compound 2

Protein detection was carried out using Compound 1 and Compound 2 synthesized in Example 1 under analysis conditions described in Example 3. After electrophoresis, the gel was first immersed in 1% Tween80 aqueous solution for 20 minutes and then immersed in a buffer containing Compound 1 (60 μg/mL) or Compound 2 (60 μg/mL) for 10 minutes.

Subsequently, the gel was transferred to and immersed in a container containing a 1% Tween80 aqueous solution for 30 minutes. Also in this case, no precipitation of Compound 1 was observed in the solutions during staining. The total time needed for treatment was 60 minutes. The gel was analyzed using a fluorescence imaging analyzer. The results are shown in FIG. 1 and Table 3. When Compound 1 was used, bands containing 2.6 ng or more of proteins could be detected. Compared with the result, the detection limit was 20 ng in the case of Compound 2.

TABLE 3

Results of protein detection

| | Lane | | | | | | | | | |
|---|---|---|---|---|---|---|---|---|---|---|
| | 1 | 2 | 3 | 4 | 5 | 6 | 7 | 8 | 9 | 10 |
| Protein (ng/band) | 167 | 83.3 | 41.7 | 20.8 | 10.4 | 5.2 | 2.6 | 1.3 | 0.7 | 0.4 |
| Detection Compound 1 | + | + | + | + | + | + | + | − | − | − |
| Compound 2 | + | + | + | + | − | − | − | − | − | − |

+: All bands could be detected.
−: At least one band could not be detected.

Regarding analysis using Compound 1, a graph showing the relationship between the protein concentration of each band and fluorescence intensity is shown in FIG. 2. In the cases of all proteins composing bands, fluorescence intensity was observed to increase as the protein concentrations were increased. Therefore, in the case of this plot, no differences due to protein type were observed.

Accordingly, it was demonstrated that Compound 1 enables successful protein detection regardless of protein type.

Evaluation of Protein Detection Using Compound 3

In a comparative example, protein detection using Compound 3 was examined.

Protein samples were prepared as follows: Sample buffer (0.0625 M Tris-HCl (pH 6.8), 5% 2-mercaptoethanol, 2% SDS, 20% glycerol, and 0.005% BPB) was added to 2.0 mg/mL commercially available BSA (PIERCE). to dilute it to concentrations of 200, 60, 30, 12, 6, 3, and 0.2 ng/µL, respectively. These protein samples were heated at 80° C. for 5 minutes and then left to stand to cool.

Conditions for electrophoresis are as follows:
Electrophoresis apparatus: ERICA XVE-001C (DRC Co., Ltd.)
Polyacrylamide gel: XV PANTERA Gel (DRC Co., Ltd.)
Buffer for electrophoresis: electrophoresis buffer attached to XV PANTERA Gel
Fluorescence imaging analyzer: LS400 (TECAN GROUP LTD)
Excitation wavelength: 543 nm; detection wavelength: 590 nm.

Each of the above prepared samples was applied to a gel at 5 µL/well (1000, 300, 150, 60, 30, 15, and 1 ng/band, respectively), followed by electrophoresis.

After electrophoresis, the gel was immediately immersed in distilled water for 20 to 30 minutes. Subsequently, the gel was transferred to another container and then a staining solution (distilled water:methanol=1:1 (v/v)) in which Compound 3 (100 µg/mL) had been dissolved was added. After 30 minutes of immersion, the gel was transferred to another container and then immersed in a wash solution (water:methanol=90:10 (v/v)) for decoloration. The gel was observed using a fluorescence imaging analyzer.

The results are shown in Table 4.

TABLE 4

Results of protein detection

| | Protein (ng/band) | | | | | | |
|---|---|---|---|---|---|---|---|
| | 1000 | 300 | 150 | 60 | 30 | 15 | 1 |
| Detection | + | + | + | + | + | − | − |

+: Band could be detected.
−: No band could be detected.

Accordingly, it was demonstrated that the protein detection sensitivity of Compound 3 was 30 ng. Therefore, compound 3 had sensitivity 10 or more times lower than that of the compound of the present invention.

Also, Compound 3 was hardly soluble in water, so that it was precipitated in the staining solution during the protein staining as described above. Hence, it was considered that the decreased concentration of Compound 3 in the staining solution resulted in insufficient protein staining. Moreover, it was difficult to completely remove excessive compounds by the washing step after staining, so that insoluble matter adhering to the gel appeared as false positive spots. In conclusion, Compound 3 was also found to be inferior to the compound of the present invention in terms of detection accuracy.

EXAMPLE 5

Embodiment of the Present Invention wherein Staining is Carried Out During Electrophoresis Compound 1 or Compound 2 were dissolved in a buffer for electrophoresis (27.2 mM Tris (hydroxymethyl)aminomethane, 192 mM glycine, and 3.5 mM sodium dodecyl sulfate (pH 8.3)) at a concentration of 15 µg/mL. With the use of the above buffer, the other conditions identical to those described in Example 3 were employed to carry out electrophoresis. After completion of electrophoresis, the gel was transferred to a container containing 1% Tween80 aqueous solution, left to stand for 40 minutes, and then analyzed using a fluorescence imaging analyzer. The results are shown in FIG. 3 and Table 5. When Compound 1 was used, bands containing 5.2 ng or more of a protein could be detected. On the other hand, proteins other than cytochrome C could not be detected in the case of Compound 2.

TABLE 5

| | Results of protein detection | | | | | | | | | |
|---|---|---|---|---|---|---|---|---|---|---|
| | Lane | | | | | | | | | |
| | 1 | 2 | 3 | 4 | 5 | 6 | 7 | 8 | 9 | 10 |
| Protein (ng/band) | 167 | 83.3 | 41.7 | 20.8 | 10.4 | 5.2 | 2.6 | 1.3 | 0.7 | 0.4 |
| Detection Compound 1 | + | + | + | + | + | + | + | − | − | − |
| Compound 2 | − | − | − | − | − | − | − | − | − | − |

+: All bands could be detected.
−: At least one band could not be detected.

Based on the results, it was demonstrated that Compound 1 enables successful protein detection even when electrophoresis and staining are carried out simultaneously.

INDUSTRIAL APPLICABILITY

The present invention makes it possible to carry out convenient, rapid, and highly sensitive protein detection regardless of protein type. Therefore, the present invention is useful in fields relating to medicine such as biochemistry and analytical chemistry, as well as in fields relating to foods.

What is claimed is:

1. An easily water-soluble fluorescent compound of formula I or a salt thereof:

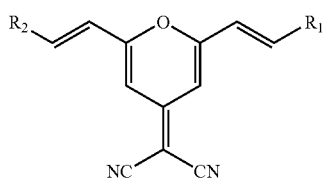

wherein $R_1$ and $R_2$, which may be same or different, are an aryl or heteroaryl group substituted with one or more sulfonic acid groups or a salt thereof.

2. The compound according to claim 1, wherein the compound is represented by formula Ia:

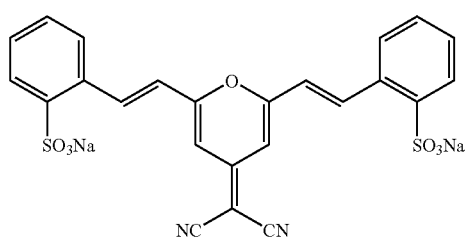

3. A method for analyzing proteins, which comprises detecting proteins with the compound according to claim 1 or 2, thereby analyzing the proteins qualitatively or quantitatively.

4. The method according to claim 3, which further comprises resolving proteins by electrophoresis.

5. The method according to claim 4, wherein resolving proteins by electrophoresis comprises:
resolving proteins on a carrier by electrophoresis; and
immersing the electrophoresis carrier in an aqueous solution containing the compound.

6. The method according to claim 4, wherein the electrophoresis is performed in the presence of a buffer comprising the compound.

7. The method according to claim 3, wherein the compound is in a solution and the method further comprises detecting in the presence of a solution comprising a detergent.

8. The method according to claim 7, wherein the detergent is a nonionic surfactant.

9. The method according to claim 7, wherein the detergent is a fatty acid polyoxyethylene sorbitan-based surfactant.

10. A reagent for protein analysis containing the compound according to claim 1 or 2.

11. The method according to claim 4, wherein the compound is in a solution and the method further comprises detecting in the presence of a solution comprising a detergent.

12. The method according to claim 11, wherein the detergent is a nonionic surfactant.

13. The method according to claim 12, wherein the detergent is a fatty acid polyoxyethylene sorbitan-based surfactant.

14. The method according to claim 5, wherein the compound is in a solution and the method further comprises detecting in the presence of a solution comprising a detergent.

15. The method according to claim 14, wherein the detergent is a nonionic surfactant.

16. The method according to claim 15, wherein the detergent is a fatty acid polyoxyethylene sorbitan-based surfactant.

* * * * *